(12) United States Patent
Lyu et al.

(10) Patent No.: US 7,396,599 B2
(45) Date of Patent: Jul. 8, 2008

(54) BINUCLEAR ORGANOMETALLIC COMPLEXES AND ORGANIC ELECTROLUMINESCENT DISPLAY DEVICE USING THE SAME

(75) Inventors: Yi-Yeol Lyu, Daejeon-si (KR); Lyong-Sun Pu, Suwon-si (KR); Das Rupasree Ragini, Suwon-si (KR); Seok Chang, Daejeon-si (KR); Young-Hun Byun, Yongin-si (KR); Eun-Sil Han, Daejeon-si (KR); Hae-Jung Son, Seoul (KR); Jong-Hyoup Lee, Seoul (KR); Tae-Yong Noh, Gunpo-si (KR)

(73) Assignee: Samsung SDI Co., Ltd., Suwon-si, Gyeonggi-do (KR)

( * ) Notice: Subject to any disclaimer, the term of this patent is extended or adjusted under 35 U.S.C. 154(b) by 505 days.

(21) Appl. No.: 11/015,677

(22) Filed: Dec. 20, 2004

(65) Prior Publication Data
US 2005/0142381 A1 Jun. 30, 2005

(30) Foreign Application Priority Data
Dec. 24, 2003 (KR) .................. 10-2003-0096193

(51) Int. Cl.
*H01L 51/54* (2006.01)
*C09K 11/06* (2006.01)

(52) U.S. Cl. ............ 428/690; 428/917; 313/504; 257/40; 257/E51.044; 546/2; 546/4; 548/101

(58) Field of Classification Search ............ None
See application file for complete search history.

(56) References Cited

U.S. PATENT DOCUMENTS

| 5,770,591 | A  | * | 6/1998 | Farrell ............ 514/187 |
| 6,824,895 | B1 | * | 11/2004 | Sowinski et al. ..... 428/690 |
| 2002/0048689 | A1 | | 4/2002 | Igarashi et al. ....... 428/690 |
| 2002/0064681 | A1 | | 5/2002 | Takiguchi et al. ..... 428/690 |
| 2002/0182441 | A1 | | 12/2002 | Lamansky et al. ..... 428/690 |
| 2003/0152802 | A1 | * | 8/2003 | Tsuboyama et al. .... 428/690 |
| 2004/0026663 | A1 | * | 2/2004 | Heuer et al. ........ 252/301.16 |

FOREIGN PATENT DOCUMENTS

WO WO 02/15645 A1 2/2002

* cited by examiner

*Primary Examiner*—Marie R. Yamnitzky
(74) *Attorney, Agent, or Firm*—Robert E. Bushnell, Esq.

(57) ABSTRACT

A binuclear organometallic complex enabling highly efficient phospholuminescence and an organic electroluminescent device using the same. The binuclear organometallic complex, which can be suitably used to form an organic layer of an organic electroluminescent device, produces luminescence in the wavelength range of 430-650 nm, and induces white electroluminescence when combined with green and red luminescent materials.

20 Claims, No Drawings

BINUCLEAR ORGANOMETALLIC COMPLEXES AND ORGANIC ELECTROLUMINESCENT DISPLAY DEVICE USING THE SAME

CLAIM OF PRIORITY

This application claims the priority of Korean Patent Application No. 2003-96193, filed on Dec. 24, 2003, in the Korean Intellectual Property Office, the disclosure of which is incorporated herein in its entirety by reference.

BACKGROUND OF THE INVENTION

1. Field of the Invention

The present invention relates to an organometallic complex capable of being used in an organic electroluminescent device, and more particularly, to a binuclear organometallic complex capable of emitting light with a wide spectrum from a blue region to a red region through triplet metal-to-ligand charge transfer (MLCT) and to an organic electroluminescent device using the same as an organic layer forming material.

2. Description of the Related Art

An organic electroluminescent (EL) device is a spontaneous light-emitting display device that generates light through the recombination of electrons and holes when an electric field is applied to thin films composed of fluorescent or phosphorescent organic compounds (organic layers). An organic EL device has various advantages including lightness, simple components and a simple manufacturing process, high resolution, wide viewing angle, high color purity, perfect reproduction of motion pictures, low power consumption, low driving voltage, and so on so that is suitable for use in portable electronic devices.

An electroluminescent layer of an organic EL device can be composed of a fluorescent material or a phosphorescent material. The fluorescent material differs from the phosphorescent material in terms of a light-emitting mechanism. The fluorescent material uses singlet excitons, and the phosphorescent material uses triplet excitons. An electroluminescent layer is composed of the fluorescent material or the phosphorescent material itself. Alternatively, the fluorescent material or the phosphorescent material is doped into an appropriate host material. In the latter case, as a result of electron excitation, singlet excitons and triplet excitons are produced in the host. Statistically, the singlet excitons and the triplet excitons are produced in a ratio of about 1:3.

A conventional organic EL devices including an electroluminescent layer composed of a fluorescent material is disadvantageous since triplet excitons are consumed by the host. However, a conventional organic EL device including an electroluminescent layer composed of a phosphorescent material are advantageous since singlet excitons and triplet excitons are both utilized to achieve an internal quantum efficiency of 100%. Thus, an organic EL device including an electroluminescent layer composed of a phosphorescent material has higher emission efficiency than an organic EL device including an electroluminescent layer composed of a fluorescent material.

The introduction of a heavy metal such as Ir, Pt, Rh, or Pd to organic molecules has led to spin-orbital coupling due to a heavy atom effect which allows a triplet state and a singlet state to coexist, thus enabling a forbidden transition, thereby allowing phospholuminescence to occur even at room temperature.

Recent developments have led to the discovery of highly efficient green and red luminescent materials using photo-electroluminescence with the internal quantum efficiency as high as 100%. In particular, a green phosphorescent material including fac-tris(2-phenylpyridine)iridium($Ir(ppy)_3$) has an external quantum efficiency of 17.6±0.5%. {Bis(2-(2'-benzo[4,5-A]thienyl)pyridinato-N,C)iridium(acetylacetonate)} ($Btp_2Ir(acac)$) has been developed as a red phosphorescent material having a high emission efficiency of 7.0±0.5%.

As described above, various materials employing various transition metal compounds containing a transition metal such as iridium or platinum have been used as highly efficient luminescent materials using phospholuminescence. However, white phosphorescent materials with high emission efficiency and low power consumption have not been developed, making it difficult to achieve a full-color display, which is, in turn, a barrier to the development of phosphorescent full-color display devices.

To address the above-described problems, the development of blue luminescent materials is under way (WO 02/15645 A1, US 2002/0048689 A1 entitled Light-emitting device and iridium complex to Igarashi Tatsuya et al. and published on Apr. 25, 2002). Also, there have been proposed organometallic complexes having bulky functional groups or functional groups having high intensity ligand fields, e.g., a cyano group, introduced thereto to increase a difference between HOMO (Highest Occupied Molecular Orbital) and LUMO (Lowest Unoccupied Molecular Orbital) energy levels by transforming the molecular geometry of the oragnometallic complexes. Other materials that have recently been developed include iridium complexes having the general formula of $Ir(ppy)_2P(ph)_3Y$, where Y is Cl or CN, as disclosed in US2002/0182441 A1 entitled Organometallic compounds and emission-shifting organic electrophosphorescence to Lamansky, Sergey et al. and published on Dec. 5, 2002, and iridium(III) complexes including a cyclometalating ligand and chelating diphosphine, chlorine and a cyano group, as disclosed in US 2002/0064681 A1 entitled Luminescence device, display apparatus and metal coordination compound to Takiguchi, Takao et al. and published on May 30, 2002.

SUMMARY OF THE INVENTION

It is therefore an object of the present invention to provide an improved material for an organic layer of an organic EL device.

It is also an object of the present invention to provide an improved organic EL device.

It is further an object of the present invention to provide a binuclear organometallic complex capable of emitting light with a wide spectrum from a blue region to a red region through triplet metal-to-ligand charge transfer (MLCT).

It is yet another object of the present invention to provide an organic electroluminescent device using the binuclear organometallic complex as an organic layer forming material.

According to an aspect of the present invention, there is provided an organometallic complex represented by Formula 1:

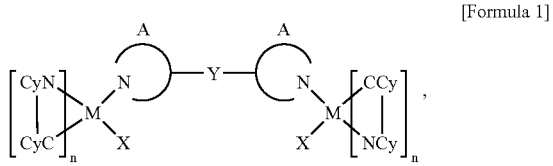

[Formula 1]

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, a substituted or unsubstituted $C_3$-$C_{60}$ heterocyclic group containing carbon bonded to M, a substituted or unsubstituted $C_3$-$C_{60}$ aryl group containing carbon bonded to M, or a substituted or unsubstituted $C_3$-$C_{60}$ heteroaryl group containing carbon bonded to M;

alternatively, CyN-CyC is represented by one of Formulas:

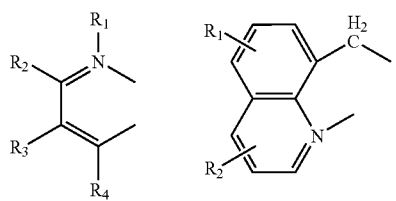

wherein each of $R_1$, $R_2$, $R_3$ and $R_4$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group;

Y is a linker connecting two mononuclear organometallic complexes to each other;

A is a group containing nitrogen bonded to M;

X is a monoanionic monodentate ligand; and n is 1 or 2.

According to another aspect of the present invention, there is provided an organic electroluminescent device comprising an organic layer interposed between a pair of electrodes, wherein the organic layer comprises the binuclear organometallic complex represented by Formula 1:

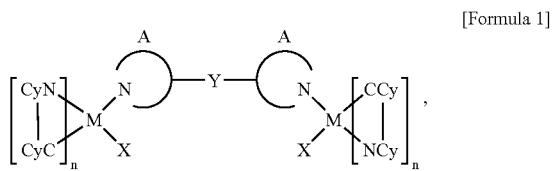
[Formula 1]

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, a substituted or unsubstituted $C_3$-$C_{60}$ heterocyclic group containing carbon bonded to M, a substituted or unsubstituted $C_3$-$C_{60}$ aryl group containing carbon bonded to M, or a substituted or unsubstituted $C_3$-$C_{60}$ heteroaryl group containing carbon bonded to M;

alternatively, CyN-CyC is represented by one of Formulas:

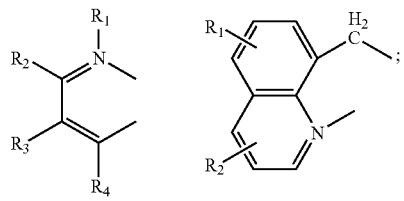

wherein each of $R_1$, $R_2$, $R_3$ and $R_4$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group;

Y is a linker connecting two mononuclear organometallic complexes to each other;

A is a group containing nitrogen bonded to M;

X is a monoanionic monodentate ligand; and n is 1 or 2.

DETAILED DESCRIPTION OF THE PREFERRED EMBODIMENTS

The present invention provides a binuclear organometallic complex capable of emitting light with a wide spectrum from a blue region to a red region through triplet metal-to-ligand charge transfer (MLCT) and an organic electroluminescent device using the same as an organic layer forming material.

According to an aspect of the present invention, there is provided an organometallic complex represented by Formula 1:

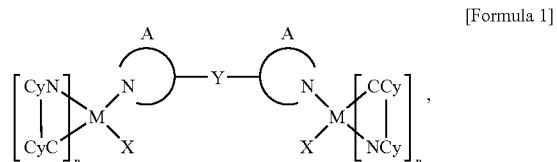
[Formula 1]

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, a substituted or unsubstituted $C_3$-$C_{60}$ heterocyclic group containing carbon bonded to M, a substituted or unsubstituted $C_3$-$C_{60}$ aryl group containing carbon bonded to M, or a substituted or unsubstituted $C_3$-$C_{60}$ heteroaryl group containing carbon bonded to M;

alternatively, CyN-CyC is represented by one of Formulas:

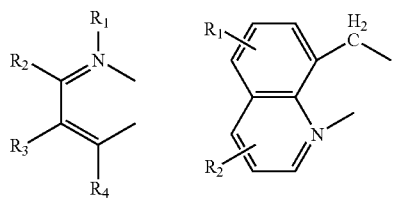

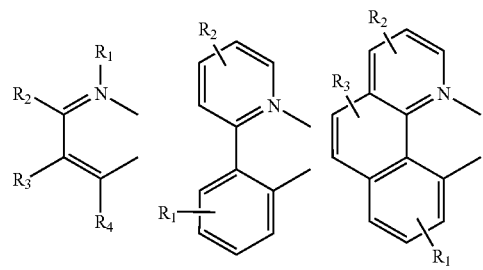

wherein each of $R_1$, $R_2$, $R_3$ and $R_4$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group;

Y is a linker connecting two mononuclear organometallic complexes to each other;

A is a group containing nitrogen bonded to M;

X is a monoanionic monodentate ligand; and n is 1 or 2.

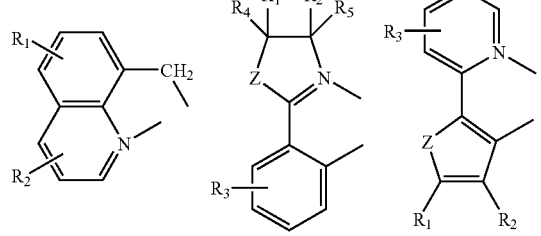

A binuclear organometallic complex according to the present invention increases a band gap between HOMO (Highest Occupied Molecular Orbital) and triplet metal-to-ligand charge-transfer (MLCT) states, enabling blue electroluminescence. The energy gap between the HOMO level and triplet MLCT state of a molecule can be increased by coordinating a bulky ligand to distort the structure of the molecule, and by adding a ligand capable of producing a strong ligand field exhibiting excellent σ-donor and π-donor capabilities. A cyanide ion (CN$^-$) can provide a strong ligand field, and reduces the HOMO energy level, leading to a blue shift in the light emission.

A cyclometalating ligand (CyN-CyC) can be represented by any one of the following formulas, but is not limited thereto.

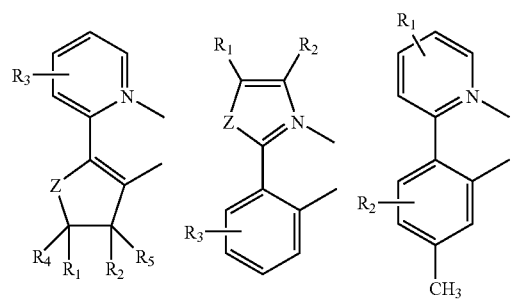

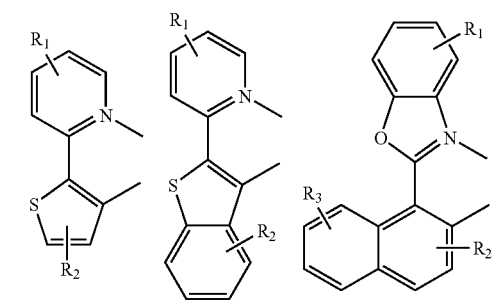

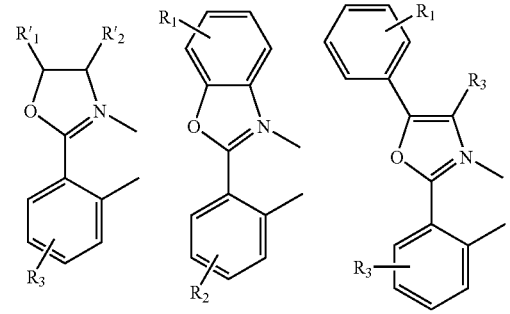

-continued

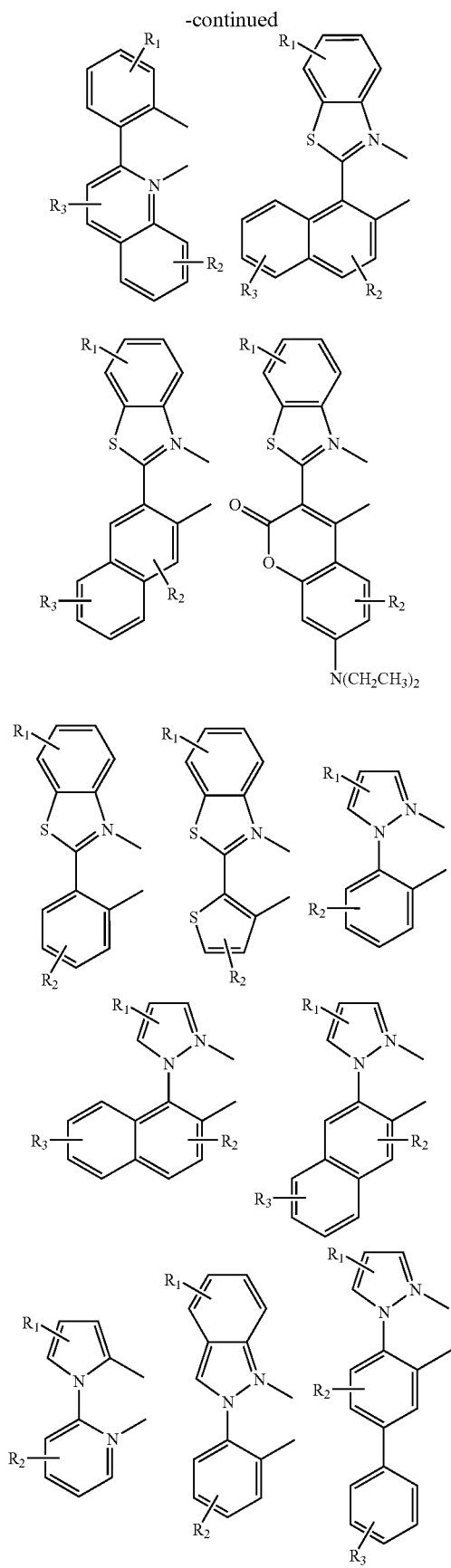

where each of $R_1$, $R_2$, $R_3$, $R_4$, and $R_5$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, or a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, or a substituted or unsubstituted $C_3$-$C_{40}$ heteroarylalkyl group; and Z is S, O, or NR$_0$ where R$_0$ is hydrogen or a $C_1$-$C_{20}$ alkyl group.

In Formula 1, the heterocyclic group and the heteroaryl group represent a cyclic group and an aryl group each containing a heteroatom such as N, O, or S, respectively.

In CyN of Formula 1, specific examples of the substituted or unsubstituted $C_3$-$C_{60}$ heterocyclic group containing nitrogen bonded to M include pyrrolidine, morpholine, thiomorpholine, thiazolidine, etc., and specific examples of the substituted or unsubstituted $C_3$-$C_{60}$ heteroaryl group containing nitrogen bonded to M include pyridine, 4-methoxy pyridine, quinoline, pyrrole, indole, pyrazine, pyrazole, imidazole, pyrimidine, quinazoline, thiazole, oxazole, triazine, 1,2,4-triazole, etc.

In CyC of Formula 1, specific examples of the substituted or unsubstituted $C_4$-$C_{60}$ carbocyclic group containing carbon bonded to M include cyclohexane, cyclopentane, etc.; specific examples of the substituted or unsubstituted $C_3$-$C_{60}$ heterocyclic group containing carbon bonded to M include tetrahydrofuran, 1,3-dioxane, 1,3-dithiane, 1,3-dithiolane, 1,4-dioxa-8-azaspiro[4,5]decane, 1,4-dioxaspiro[4,5]decan-2-one, etc.; specific examples of the substituted or unsubstituted $C_3$-$C_{60}$ aryl group containing carbon bonded to M include phenyl, 1,3-(benzodioxole), biphenyl, naphthalene, anthracene, azulene, etc.; and specific examples of the substituted or unsubstituted $C_3$-$C_{60}$ heteroaryl group containing carbon bonded to M include thiophene, furan2(5H)-firanone, pyridine, coumarin, imidazole, 2-phenylpyridine, 2-benzothiazole, 2-benzoxazole, 1-phenylpyrazole, 1-naphthylpyrazolel-naphthylpyrazole, 5-(4-methoxyphenyl)pyrazole, 2,5-bisphenyl-1,3,4-oxadiazole, 2,3-benzofuran2-(4-biphenyl)-6-phenyl benzooxazole, etc.

In Formula 1, the respective substituents of CyN-CyC are interconnected to form a substituted or unsubstituted 4- to 7-membered cyclic group or a substituted or unsubstituted 4- to 7-membered heterocyclic group, in particular, a fused 4- to 7-membered cyclic or heterocyclic group. The cyclic group or the hetero cyclic group is a $C_1$-$C_{30}$ cycloalkyl group, a $C_1$-$C_{30}$ heterocycloalkyl group, a $C_6$-$C_{30}$ aryl group, or a $C_4$-$C_{30}$ heteroallyl group, and each cyclic group or heterocyclic group can be substituted by one or more substituents. The term "hetero" used herein is intended to encompass heteroatoms such as N, O, P, and S.

The substituent is a halogen atom, —OR$_1$', —N(R$_1$')$_2$, —P(R$_1$')$_2$, —POR$_1$', —PO$_2$R$_1$', —PO$_3$R$_1$', —SR$_1$', —Si(R$_1$')$_3$, —B(R$_1$')$_2$, —B(OR$_1$')$_2$, —C(O)R$_1$', —C(O)OR$_1$', —C(O)N(R$_1$'), —CN, —NO$_2$, —SO$_2$, —SOR$_1$', —SO$_2$R$_1$', or —SO$_3$R$_1$', and R$_1$' is defined in the same manner as R.

A represents a monocationic monodentate ligand containing nitrogen bonded to M; and X represents a monoanionic monodentate ligand such as F, Cl, Br, I, CN, CN(R), SCN, or OCN.

Non-limiting examples of A (i.e., the group containing nitrogen bonded to M) include a compound derived from one selected from the group consisting of substituted or unsubstituted triethylamine, propylamine, cyclohexylamine, pyrrolidine, pyrroline, piperidine, pyrimidine, indole, azaindole, carbazole, indazole, norharman, harman, aniline, imidazole, oxazole, thiazole, pyrazole, pyrrole, benzimidazole, benzotriazole, benzoxazole, benzothiazole, benzoselenazole, benzothiadiazole, isoxazole, isothiazole, oxadiazole, thiadiazole, anthranyl, triazine, benzisoazole, pyrazine, quinoline, benzoquinoline, acridine, thiazoline, quinuclidine, imidazoline, oxazoline, thiazoline, and isoquinoline.

Y is a linker that links two organometallic complexes is a C$_1$-C$_{20}$ alkylene group; a C$_6$-C$_{20}$ arylene group; a C$_1$-C$_{20}$ heteroalkylene group; a C$_2$-C$_{20}$ heteroarylene group; a C$_3$-C$_{20}$ heteroarylalkylene group; a carbonyl group; or a group derived from symmetrical triarylamines, asymmetrical triarylamines, phenylenevinylenes, polyfluorenes, polythiophenes, vinylcarbazoles, ethylene dioxythiophenes, silanes, siloxanes, or derivatives of these. If Y is a group derived from siloxane derivatives, it is preferable that a number of a siloxane moiety (Si(R')(R")—O— where each of R' and R" is an alkyl group) included therein is less than or equal to 15. Examples of a siloxane derivative containing less than or equal to 15 siloxane moieties include disiloxane, trisiloxane, tetrasiloxane, and pentasiloxane.

Y may be a dimethylsilyl group, a tetramethyldisiloxyl group, a hexamethyltrisiloxyl group, an octamethyltetrasiloxyl group, an ethyl group, a propyl group, a butyl group, a pentyl group, a hexyl group, a heptyl group, an octyl group, a penyl group, a tetrafluorophenyl group, a bipenylene group, a naphthylene group, a cyclohexylene group, or a divalent group derived from the group consisting of 1,2-bis(4-pyridyl)ethane, 1-Carbazolyl-4-(1-naphthylphenylamino)benzene (NαCP), 1-Carbazolyl-4-(diphenylamino)benzene (DCP), 1-Carbazolyl-4-(phenyl-m-tolylamino)benzene (TCP), 1-Carbazolyl-4-(iminodibenzyl)benzene (BCP), 1-Carbazole-4-(iminostilbenyl)benzene (SCP), 1-(1-Naphthylphenylamino)-4-(diphenylamino)benzene (DNαP), 1-(1-Naphthylphenylamino)-4-(phenyl-m-tolylamino)benzene (TNαP), 1-(1-Naphthylphenylamino)-4-(iminodibenzyl)benzene (BNαP), 1-(1-Naphthylphenylamino)-4-(iminostilbenyl)benzene (SNαP), 1-(Diphenylamino)-4-(phenyl-m-tolylamino)benzene (TDP), 1-(Diphenylamino)-4-(iminodibenzyl)benzene (BDP), 1-(Diphenylamino)-4-(iminostilbenyl)benzene (SDP), 1-(Phenyl-m-tolylamino)-4-(iminodibenzyl)benzene (BTP), 1-(Phenyl-m-tolylamino)-4-(iminostilbenyl)benzene (STP), 1-(Iminodibenzyl-4-(iminostilbenyl)benzene (SBP), 4-Carbazolyl-4'-(2-naphthylphenylamino)biphenyl (NbCB), 4-Carbazolyl-4'-(diphenylamino)biphenyl (DCB), 4-Carbazolyl-4'-(phenyl-m-tolylamino)biphenyl (TCB), 4-Carbazolyl-4'-(iminodibenzyl)biphenyl (BCB), 4-Carbazolyl-4'-(iminostilbenyl)biphenyl (SCB), 4-(1-Naphthylphenylamino)-4'-(2-naphthylphenylamino)biphenyl (NbNaB), 4-(1-Naphthylphenylamino)-4'-(diphenylamino)biphenyl (DNaB), 4-(1-Naphthylphenylamino)-4'-(phenyl-m-tolylamino)biphenyl (TNaB), 4-(1-Naphthylphenylamino)-4'-(iminodibenzyl)biphenyl (BNaB), 4-(1-Naphthylphenylamino)-4'-(iminostilbenyl)biphenyl (SNaB), 4-(Diphenylamino)-4'-(phenyl-m-tolylamino)biphenyl (TDB), 4-(Diphenylamino)-4'-(iminodibenzyl)biphenyl (BDB), 4-(Diphenylamino)-4'-(iminostilbenyl)biphenyl (SDB), 4-(Phenyl-m-tolylamino)-4'-(iminodibenzyl)biphenyl (BTB), 4-(Phenyl-m-tolylamino)-4'-(iminostilbenyl)biphenyl (STB), 4-(Iminodibenzyl)-4'-(iminostilbenyl)biphenyl (SBB), 1,4-Bis(carbazolyl)benzene (CCP)], 1,4-Bis(1-naphthylphenylamino)benzene (NaNaP), 1,4-Bis(2-naphthylphenylamino)benzene (NbNbP), 1,4-Bis(diphenylamino)benzene (DDP), 1,4-Bis(phenyl-m-tolylamino)benzene (TTP), 1,4-Bis(iminobenzyl)benzene (BBB), 1,4-Bis(iminostilbenyl)benzene (SSP), 1,4-Bis(2-naphthylphenylamino)biphenyl (NbNbB), 1,4-Bis(diphenylamino)biphenyl (DDB), 1,4-Bis(phenyl-m-tolylamino)biphenyl (TTB), 1,4-Bis(iminostilbenyl)biphenyl (SSB), poly(3-cyclohexyl-2-methylthiophene) [PCHMT], poly(3-cyclohexylthiophene) [PCHT], poly(3-(4-octylphenyl)-2,2'-bithiophene) [PTOPT], poly(3-octylphenylthiophene) [POPT], poly dialkoxy-(p-phenylene vinylene) [RO-PPV]}, poly cyano-(p-phenylene vinylene) [CN-PPV], poly(2-methoxy 5-(2'-ethylhexyloxy)-1,4-phenylenevinylene) [MEH-PPV], poly dialkoxy-p-phenylene [RO-PPP], poly fluoroalkyl-p-phenylene [FA-PPP], poly(p-phenylphenylene vinylene) [PPPV], poly(9-vinylcarbazole) [PVK], poly(3,4-ethylene dioxythiophene) [PEDOT], poly (3,4-ethylene dioxythiophene) doped with poly(styrene sulfonate) [PEDOT:PSS], poly dialkyl fluorene [PDAF], poly spirofluorene [PSF], poly diethyl silane [PDES], poly methylphenyl silane [PMPS], poly dicyclohexyl silane [PCHS], and poly di(4-n-butylphenyl)silane [PBPE].

The binuclear organometallic complex may be represented by Formula 8 or Formula 9 below:

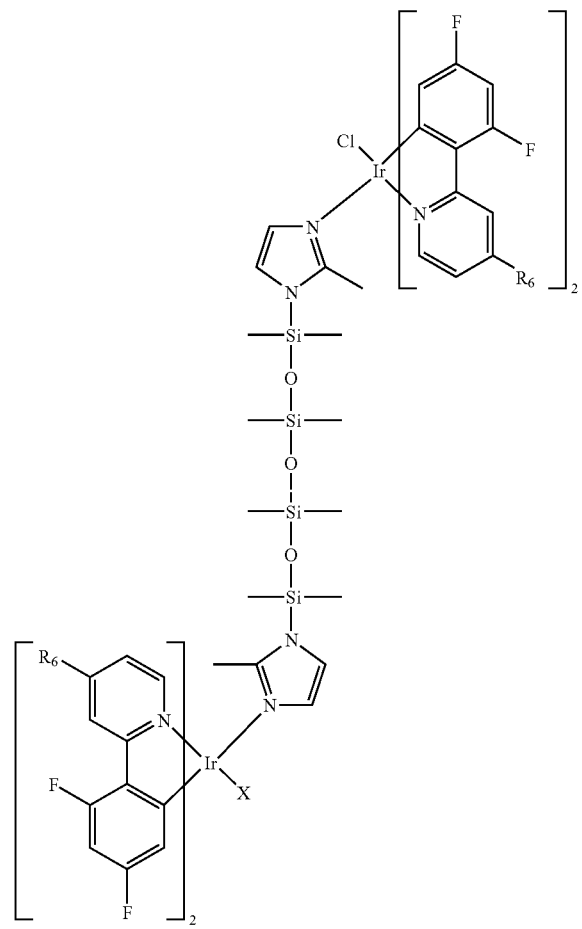

Formula 8 wherein $R_6$ is a $C_{1-12}$ alkyl group or $-N(R)_2$ where R is a $C_{1-12}$ alkyl group; and X is F, Cl, Br, I, CN, CN(R), SCN, or OCN, Formula 9

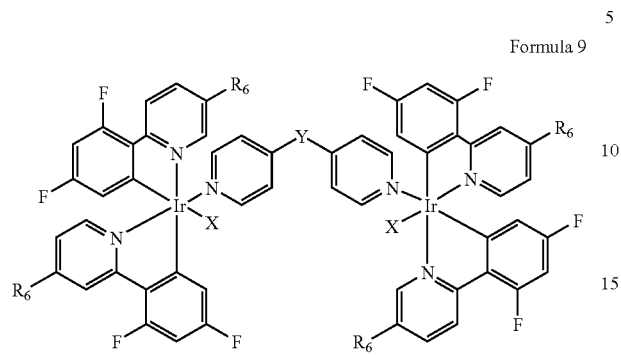

wherein $R_6$ is a $C_{1-12}$ alkyl group or $-N(R)_2$ where R is a $C_{1-12}$ alkyl group; X is F, Cl, Br, I, CN, CN(R), SCN, or OCN; and Y is a $C_{1-12}$ alkylene group, a $C_{6-20}$ arylene group, a $C_{3-20}$ heteroarylene group, or a carbonyl group.

The binuclear organometallic complex represented by Formula 1 may be a compound selected from the compounds represented by Formulas 3 through 7:

Formula 3

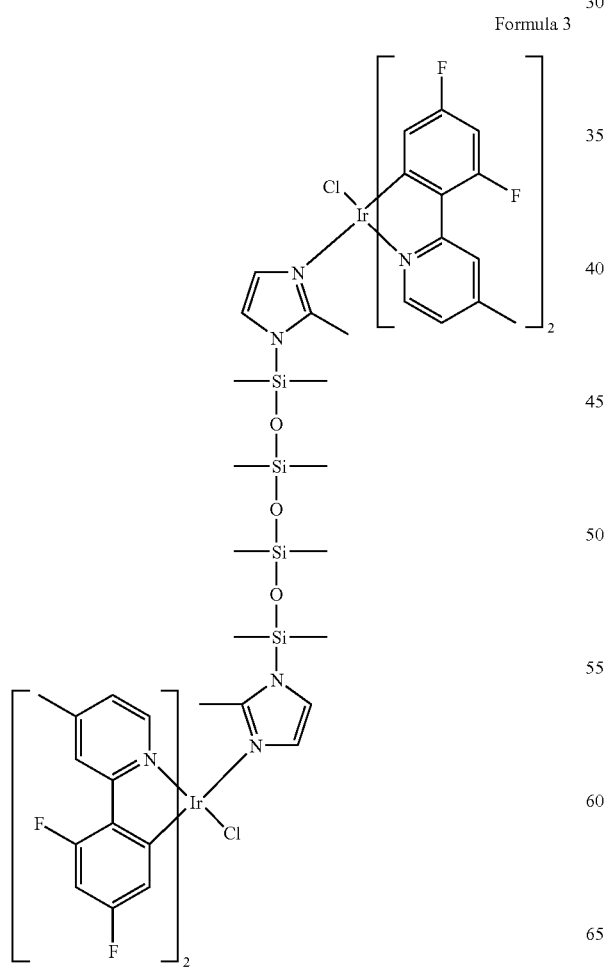

Formula 4

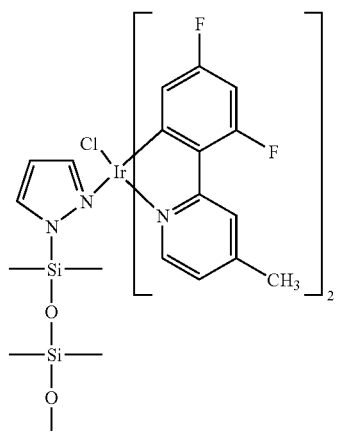

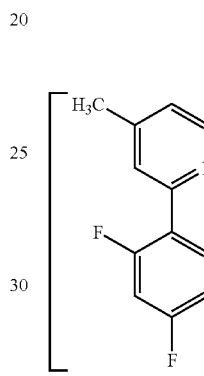

Formula 5

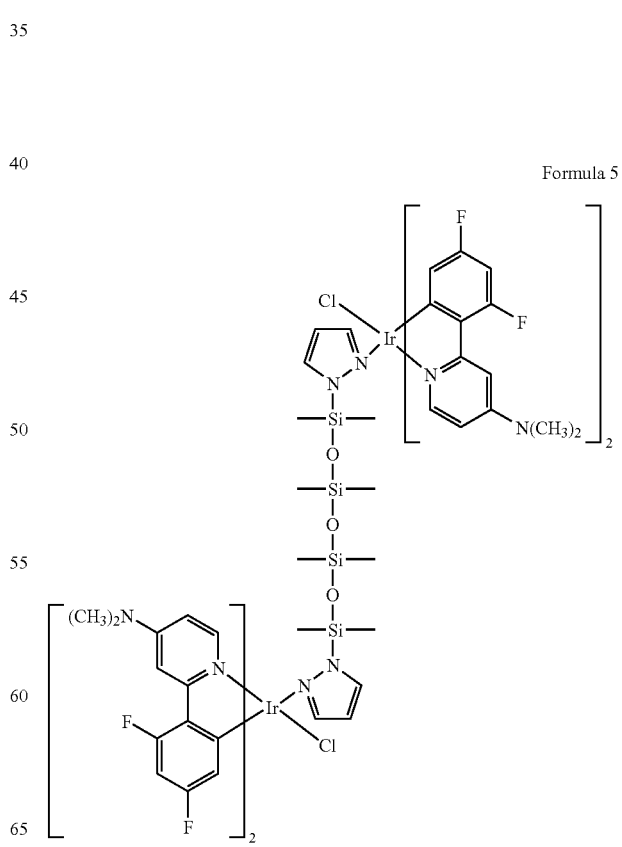

-continued

Formula 6

Formula 7

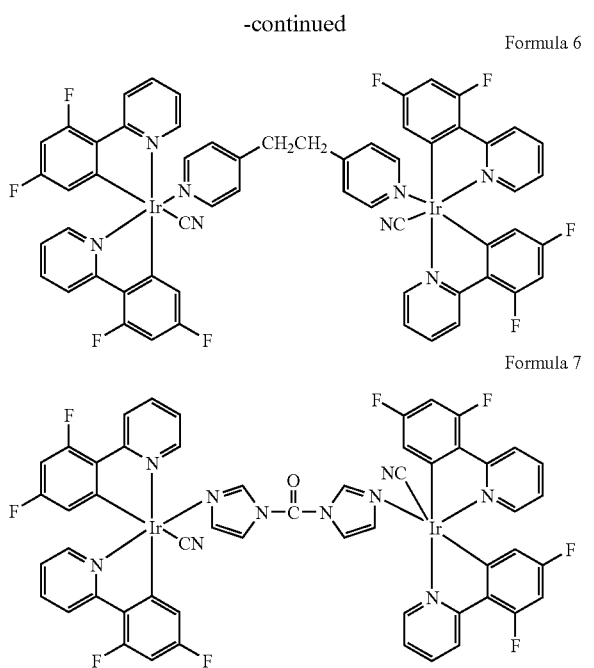

The binuclear organometallic complex is represented by Formula 1 can be prepared by a method in which a [Ir(C^N)$_2$Cl]$_2$ derivative is used as a starting material for providing cyclometalating moiety, as reported by Watts et al (See F. O. Garces, R. J. Watts, Inorg. Chem. (35), 2450, 1988, which is incorporated herein by reference). Alternatively, a mononuclear organometallic complex can be synthesized, and then reacted with a compound capable of bonding a ligand to form a binuclear organometallic complex.

The organic EL device according to the present invention is manufactured by forming an organic layer, in particular, a electroluminescent layer, comprising the binulcear organometallic complex represented by Formula 1. The binuclear organometallic complex represented by Formula 1 is used as a phosphorescent dopant material, which is a material for forming the electroluminescent layer, and exhibits excellent emission characteristics in the blue range.

When the binuclear organometallic complex represented by Formula 1 is used as a phosphorescent dopant, the organic layer may further comprise at least a compound selected from the group consisting of at least one polymer host, a mixture of a polymer host and a low molecular weight molecule host, a low molecular weight molecule host, and non-luminous polymer matrix. The polymer host, the low molecular weight molecule host and the non-luminous polymer matrix may be any conventional materials for forming a electroluminescent layer of an organic EL device. Examples of the polymer host include, but are not limited to, poly(vinylcarbazole)(PVK), and polyfluorene. Examples of the low molecular weight molecule host include, but are not limited to, CBP(4,4'-N,N'-dicarbazole-biphenyl), 4,4'-bis[9-(3,6-biphenylcarbazolyl)]-1-1,1'-biphenyl{4,4'-bis[9-(3,6-biphenylcarbazolyl)]-1-1,1'-biphenyl}, 9,10-bis[(2',7'-t-butyl)-9',9'''-spirobifluorenylanthracene, and tetrafluorene. Examples of the non-luminous polymer matrix include, but are not limited to, polymethacrylate and polystyrene.

The concentration of the binuclear organometallic complex represented by Formula 1 may be 1 to 30 parts by weight based on 100 parts by weight of the total weight of the electroluminescent layer forming material. Methods of introducing the binuclear organometallic complex into the electroluminescent layer include printing, coating, ink-jet printing, and electron-beam application. In addition, the binuclear organometallic complex represented by Formula 1 can induce white electroluminescence when combined with green or red luminescent materials. The thickness of the organic layer may be in the range of about 30 to 100 nm. The term "organic layer" used herein refers to a layer composed of an organic compound formed interposed a pair of electrodes in an organic electroluminescent device, for example, a electroluminescent layer, an electron transport layer, or a hole transport layer. The organic electroluminescent device can have a structure selected from the group consisting of an anode/electroluminescent layer/anode structure, an anode/buffer layer/electroluminescent layer/cathode structure, an anode/hole transport layer/electroluminescent layer/cathode structure, an anode/buffer layer/hole transport layer/electroluminescent layer/cathode structure, an anode/buffer layer/hole transport layer/electroluminescent layer/electron transport layer/cathode structure, and an anode/buffer layer/hole transport layer/electroluminescent layer/hole blocking layer/cathode structure, but is not limited to these structures.

The buffer layer may be composed of any materials commonly used in the art, such as copper phthalocyanine, polythiophene, polyaniline, polyacetylene, polypyrrole, polyphenylene vinylene, and derivatives thereof, but is not limited thereto.

The hole transport layer may be composed of any materials commonly used in the art, such as polytriphenylamine, but is not limited thereto.

The electron transport layer may be composed of any materials commonly used in the art, such as polyoxadiazole, but is not limited thereto.

The hole blocking layer may be composed of any materials commonly used in the art, such as LiF, BaF$_2$, and MgF$_2$, but is not limited thereto.

The organic electroluminescence device according to the present invention can be manufactured using a method of manufacturing an organic electroluminescence device in which conventional light-emitting materials are used, without the use of specific apparatus and methods.

The binuclear organometallic complex can emit light with wavelengths in a range from 400 to 650 nm. Light emitting diodes using the binuclear organometallic complex can be used in applications such as light sources for a full color display illumination, backlighting, signboards, optical communication, and indoor decoration.

Hereinafter, the present invention will now be described in more detail with reference to the following Examples. These examples are for illustrative purposes only and are not intended to limit the scope of the invention.

PREPARATION EXAMPLE 1

Synthesis of F$_2$PPY Dimer

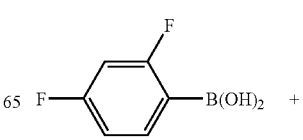

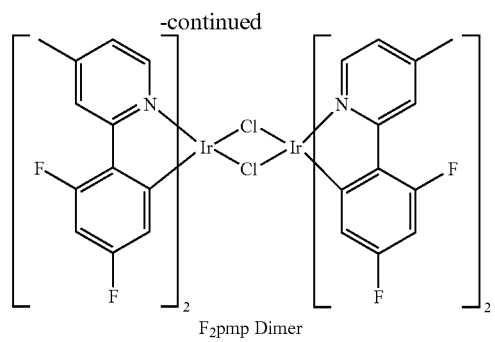

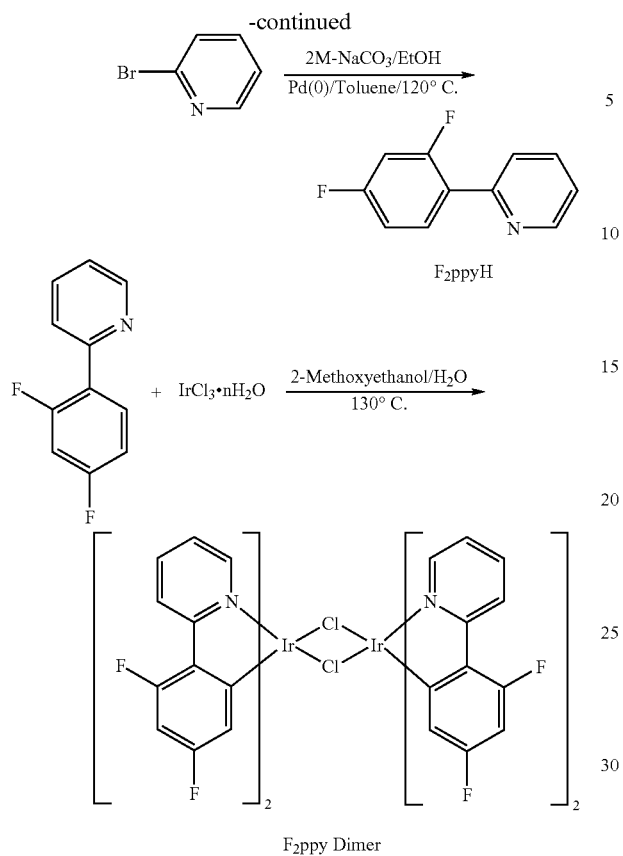

19.85 g (1.25×10⁴ mmol) of 2-bromopyridine, 25.00 g (1.58×10⁴ mmol) of 2,4-difluorophenyl boronic acid, 100 mL toluene, 48 mL of ethanol, and 2M sodium carbonate solution were added to a 500 mL flask, and stirred under a nitrogen atmosphere at room temperature. Then, 4.53 g (3.92 mmol) of tetrakis(triphenylphosphine)palladium(0) was added to the reaction mixture and refluxed for 15 hours under a nitrogen atmosphere without exposure to light.

After the reaction was completed, the temperature of the reaction mixture was adjusted to room temperature, and the reaction mixture was extracted using ethyl acetate and water and isolated by column chromatography eluting with 10:1 (by volume) toluene/hexane, thus producing a light brown liquid ($F_2ppyH$).

A 2-(4,6-difluorophenylpyridine)monomer prepared above, and $IrCl_3 \cdot nH_2O$ were used to prepare a $F_2ppy$ dimer in a yellow powder state. The preparation method described in J. Am. Chem. Soc., 1984, 106, 6647-6653 was incorporated herein by reference.

$^1$H-NMR(CD$_2$Cl$_2$, ppm): 9.1 [d, 4H], 8.3 [d, 4H], 7.9 [t, 4H], 6.9 [m, 4H], 6.5 [m, 4H], 5.3 [d, 4H].

PREPARATION EXAMPLE 2

Synthesis of $F_2$PMP Dimer

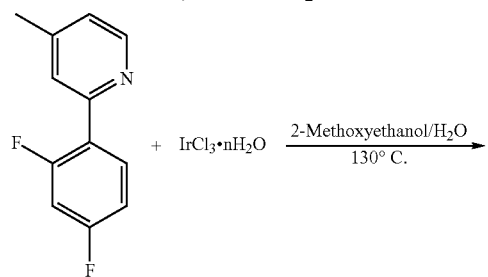

A $F_2$pmp dimer was synthesized in the same manner as in Preparation Example 1, except that 2-bromo-4-methylpyridine was used instead of 2-bromopyridine.

$^1$H-NMR(CD$_2$Cl$_2$, ppm): 8.9 [d, 4H], 8.1 [s, 4H], 6.6 [d, 4H], 6.3 [m, 4H], 5.3 [d, 4H], 2.6 [s, 12H]

PREPARATION EXAMPLE 3

Synthesis of DMAF$_2$PPY Dimer

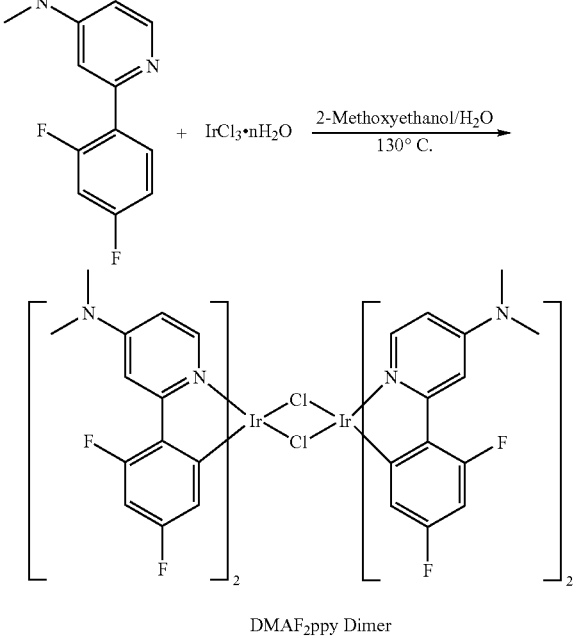

A DMAF$_2$ppy dimer was synthesized in the same manner as in Preparation Example 1, except that 2-bromo-4-(N,N'-dimethyl)pyridine was used instead of 2-bromopyridine.

$^1$H-NMR(CD$_2$Cl$_2$, ppm): 8.7 [d, 4H], 7.5 [t, 4H], 6.3 [m, 4H], 6.1 [m, 4H], 5.4 [d, 4H], 3.2 [s, 24H]

PREPARATION EXAMPLE 4

Synthesis of Binuclear Organomatellic Complex Represented by Formula 3

0.4 mmol of the $F_2$pmp dimer, and 0.88 mmol of 1-methyl imidazole were placed in a 250 mL flask, dissolved in 30 mL methylene chloride under a nitrogen atmosphere and reacted at room temperature for 10 hours.

After the reaction was completed, the reaction mixture was passed through a pad of celite for filtration, followed by precipitating in 100 mL hexane, producing a mononuclear organometallic complex in a yellow powder state. 0.5 mmol of the mononuclear organometallic complex was dissolved in 20 ml methylene chloride in a reactor, 2.5 mmol potassium cyanide dissolved in 15 ml methanol was added thereto, and the result was stirred at room temperature for 3 hours. After the reaction was completed, the reaction solution was filtered through a pad of celite and the filtrate was precipitated in hexane, thereby acquiring a yellow powder. 0.03 mmol of the acquired yellow powder and 0.33 mmol of triethylamine were placed in a 250 mL flask, and then 0.15 mmol of 1,7-dichlorooctamethyltetrasiloxane was slowly added thereto at 0□. Then, the mixture solution was reacted at room temperature for 10 hours. After the reaction was completed, the reaction solution was passed through a pad of celite for filtration, and then a reaction solvent and a volatile material were removed from the filtrate under reduced pressure. The resultant mixture was completely dissolved in 10 mL tetrahydrofuran. The solution was filtered using a 0.2 µm filter to remove from solid components, and then the filtered solution was precipitated by adding 50 mL of hexane to acquire a binuclear organometallic complex in a yellow powder state. The resultant yellow powder was purified by silica gel column chromatography using a 10:1 mixed solvent of methylene chloride and acetone. The final product was identified by $^1$H-NMR spectroscopy.

$^1$H-NMR(CD$_2$Cl$_2$, ppm): 9.5 [d, 2H], 8.1 [s, 2H], 8.0 [s, 2H], 7.88 [s, 2H], 7.85 [d, 2H], 7.0 [d, 2H], 6.9 [d, 2H], 6.8 [s, 2H], 6.7 [s, 2H], 6.3-6.5 [m, 4H], 5.7 [m, 4H], 3.6 [s, 6H], 2.5 [d, 12H], 0.13 [s, 12H], 0.09 [s, 12H]

The emission characteristics of the obtained binuclear organometallic complex represented by Formula 3 were determined in the following manner.

First, the binuclear organometallic complex represented by Formula 3 was dissolved in methylene chloride to prepare a 10$^{-4}$ M solution, and then emission characteristics of the compound being in the solution state were evaluated.

The results showed that the binuclear organometallic complex represented by Formula 3 had an emission wavelength peak at 455.8 nm with a shoulder at 482.5 nm, and that the CIE (Commission Internationale de l'Eclairage) color coordinate (x, y) of the binuclear organometallic complex represented by Formula 3 was (0.147, 0.195).

PREPARATION EXAMPLE 5

Synthesis of Binuclear Organometallic Complex Represented by Formula 4

The binuclear organometallic complex represented by Formula 4 was synthesized in the same manner as in Preparation Example 4, except that pyrazole was used instead of 1-methylimidazole, and the final product was identified by $^1$H-NMR spectroscopy.

$^1$H-NMR(CD$_2$Cl$_2$, ppm): 10.8 [s, 2H], 9.66 [d, 2H], 8.1 [s, 2H], 8.0 [s, 2H], 7.77 [s, 2H], 7.55 [d, 2H], 7.13 [d, 2H], 6.96 [d, 2H], 6.7 [s, 2H], 6.5 [m, 2H], 6.4 [m, 2H], 6.25 [s, 2H], 5.8 [d-d, 2H], 5.6 [d-d, 2H], 2.55 [d, 12H], 0.13 [s, 12H], 0.09 [s, 12H]

The emission characteristics of the obtained binuclear organometallic complex represented by Formula 4 were determined in the same manner as in Preparation Example 4. The binuclear organometallic complex represented by Formula 4 had an emission wavelength peak at 468 nm with a shoulder at 490 nm in a solution state. The CIE color coordinate (x, y) of the binuclear organometallic complex represented by Formula 4 was (0.1443, 0.2669).

PREPARATION EXAMPLE 6

Synthesis of Binuclear Organometallic Complex Represented by Formula 5

The binuclear organometallic complex represented by Formula 5 was synthesized in the same manner as in Preparation Example 4, except that the DMAF$_2$ppy dimer, rather than the F$_2$pmp dimer, was used, and the final product was identified by $^1$H-NMR spectroscopy.

$^1$H-NMR(CD$_2$Cl$_2$, ppm): 10.8 [s, 2H], 9.25 [d, 2H], 7.74 [s, 2H], 7.48 [t, 2H], 7.42 [t, 2H], 718 [d, 2H], 6.7 [s, 2H], 6.56 [d-d, 2H], 6.39-6.42 [m, 4H], 6.20-6.24 [m, 4H], 5.03 [d-d, 2H], 5.74 [d-d, 2H], 3.1 [d, 24H], 0.13 [s, 12H], 0.09 [s, 12H]

The emission characteristics of the obtained binuclear organometallic complex represented by Formula 5 were determined in the same manner as in Preparation Example 4. The binuclear organometallic complex represented by Formula 5 had an emission wavelength peak at 458 nm with a shoulder at 480 nm in a solution state. The CIE color coordinate (x, y) of the binuclear organometallic complex represented by Formula 5 was (0.1445, 0.1858).

PREPARATION EXAMPLE 7

Synthesis of Binuclear Organometallic Complex Represented by Formula 6

0.5 mmol of the F$_2$ppy dimer, and 0.250 mmol of 1,2-bis (4-pyridyl)ethane were placed in a 250 mL multi-necked flask, dissolved in 30 mL methylene chloride under a nitrogen atmosphere, and reacted at room temperature for 10 hours. After the reaction was completed, the reaction mixture was passed through a pad of celite for filtration. Then, the filtrate was precipitated in 100 mL hexane, thus producing in a yellow powder state a binuclear organometallic complex containing a ligand substituted with 1,2-bis(4-pyridyl)ethane. 0.5 mmol of the binuclear organometallic complex was dissolved in 20 ml methylene chloride in a reactor, 2.5 mmol potassium cyanide dissolved in 15 ml methanol was added thereto, and the result was stirred at room temperature for 3 hours. After the reaction was completed, the reaction solution was filtered by passing through a pad of celite, and a reaction solvent and a volatile material were removed from the filtered solution under reduced pressure. The resultant mixture was completely dissolved in 10 mL tetrahydrofuran. The solution was filtered using a 0.2 µm filter to remove from solid components, and then precipitated in 50 mL hexane to acquire a binuclear organometallic complex in a yellow powder state. The resultant yellow powder was purified by silica gel column chromatography using a 10:1 mixed solvent of methylene chloride and acetone. The final product was identified by $^1$H-NMR spectroscopy.

$^1$H-NMR(CD$_2$Cl$_2$, ppm): 9.5 [d, 2H], 8.1 [s, 2H], 8.0 [s, 2H], 7.88 [s, 2H], 7.85 [d, 2H], 7.0 [d, 2H], 6.9 [d, 2H], 6.8 [s, 2H], 6.7 [s, 2H], 6.3-6.5 [m, 4H], 5.7 [m, 4H], 3.6 [s, 6H], 2.5 [d, 12H], 0.13 [s, 12H], 0.09 [s, 12H]

The emission characteristics of the obtained binuclear organometallic complex represented by Formula 6 were determined in the following manners.

First, the binuclear organometallic complex represented by Formula 6 was dissolved in methylene chloride to prepare a 10$^{-4}$ M solution, and then emission characteristics of the binuclear organometallic complex represented by Formula 6 were evaluated in the solution state.

The results showed that the binuclear organometallic complex represented by Formula 6 obtained in the above-mentioned manner had an emission wavelength peak at 457 nm with a shoulder at 478 nm, and that the CIE color coordinate (x, y) of the binuclear organometallic complex represented by Formula 6 was (0.146, 0.188).

PREPARATION EXAMPLE 8

Synthesis of Binuclear Organometallic Complex Represented by Formula 7

The binuclear organometallic complex represented by Formula 7 was synthesized in the same manner as in Preparation Example 7, except that 1,1'-Carbonyldiimidazole was used instead of 1,2-bis(4-pyridyl) and the final product was identified by $^1$H-NMR spectroscopy.

$^1$H-NMR(CD$_2$Cl$_2$, ppm): 10.8 [s, 2H], 9.25 [d, 2H], 7.74 [s, 2H], 7.48 [t, 2H], 7.42 [t, 2H], 718 [d, 2H], 6.7 [s, 2H], 6.56 [d-d, 2H], 6.39-6.42 [m, 4H], 6.20-6.24 [m, 4H], 5.93 [d-d, 2H], 5.74 [d-d, 2H], 3.1 [d, 24H], 0.13 [s, 12H], 0.09 [s, 12H]

The emission characteristics of the obtained binuclear organometallic complex represented by Formula 7 were determined in the same manner as in Preparation Example 7. The binuclear organometallic complex represented by Formula 7 had an emission wavelength peak at 458 nm with a shoulder at 485 nm in a solution state. The CIE color coordinate (x, y) of the binuclear organometallic complex represented by Formula 7 was (0.145, 0.262).

The binuclear organometallic complex represented by Formula 1 can efficiently emit light with a wavelength in a blue range to a red range using triplet MLCT. The organometallic complex is suitably used to form an organic layer of an organic electroluminescent device, and can emit light in a wavelength range of 400-650 nm. Also, the binuclear organometallic complex may be used to produce white electroluminescence when combined with green and red luminescent materials.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An organometallic complex represented by Formula 1:

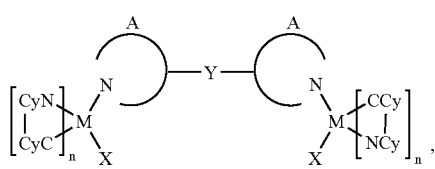

(1)

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is selected from the group consisting of a substituted or unsubstituted $C_4$-$C_{60}$ carbocyclic group containing carbon bonded to M, a substituted or unsubstituted $C_3$-$C_{60}$ heterocyclic group containing carbon bonded to M, a substituted or unsubstituted $C_3$-$C_{60}$ aryl group containing carbon bonded to M, and a substituted or unsubstituted $C_3$-$C_{60}$ heteroaryl group containing carbon bonded to M;

alternatively, CyN-CyC is represented by one of Formulas:

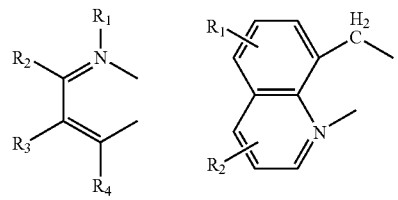

wherein each of $R_1$, $R_2$, $R_3$, and $R_4$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group;

Y is a linker connecting two mononuclear organometallic complexes to each other;

A is a group containing nitrogen bonded to M;

X is a monoanionic monodentate ligand; and n is 1 or 2.

2. The organometallic complex of claim 1, wherein the CyN-CyC is represented by one of the following formulas:

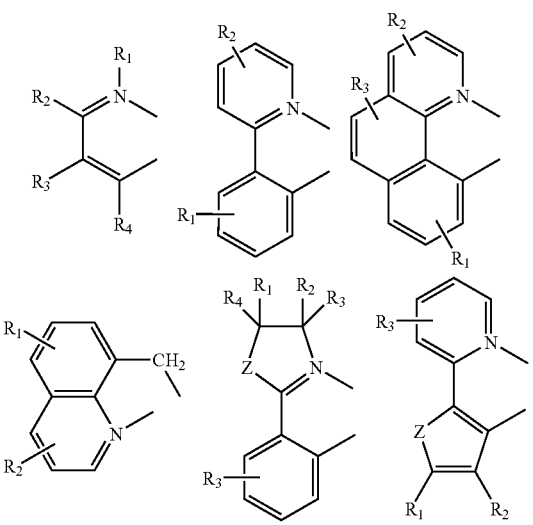

-continued
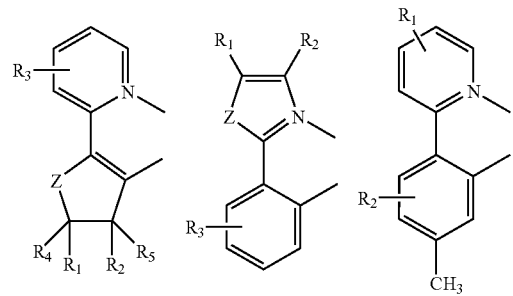
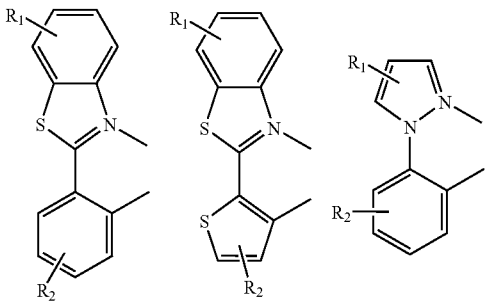

wherein each of $R_1$, $R_2$, $R_3$, $R_4$, and $R_5$ is independently a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$ where R$_0$ is hydrogen or a $C_1$-$C_{20}$ alkyl group.

3. The organometallic complex of claim 1, wherein A is derived from one selected from the group consisting of substituted or unsubstituted triethylamine, propylamine, cyclohexylamine, pyrrolidine, pyrroline, piperidine, pyrimidine, indole, azaindole, carbazole, indazole, norharman, harman, aniline, imidazole, oxazole, thiazole, pyrazole, pyrrole, benzimidazole, benzotriazole, benzoxazole, benzothiazole, benzoselenazole, benzothiadiozole, isoxazole, isothiazole, oxadiazole, thiadiazole, anthranyl, triazine, benzisoxazole, pyrazine, quinoline, benzoquinoline, acridine, thiazoline, quinuclidine, imidazoline, oxazoline, thiazoline, and isoquinoline.

4. The organometallic complex of claim 1, wherein X is selected from the group consisting of F, Cl, Br, I, CN, SCN, and OCN.

5. The organometallic complex of claim 1, wherein Y is a $C_1$-$C_{20}$ alkylene group, a $C_6$-$C_{20}$ arylene group, a $C_1$-$C_{20}$ heteroalkylene group, a $C_2$-$C_{20}$ heteroarylene group, a $C_3$-$C_{20}$ heteroarylalkylene group, a carbonyl group, or a group derived from compounds selected from the group consisting of symmetrical triarylamines, asymmetrical triarylamines, phenylenevinylenes, polyfluorenes, polythiophenes, vinylcarbazoles, ethylene dioxythiophenes, silanes, siloxanes, and derivatives of thereof.

6. The organometallic complex of claim 1, wherein M is Ir or Pt.

7. The organometallic complex of claim 1, wherein said organometallic complex is represented by Formula 8 or Formula 9:

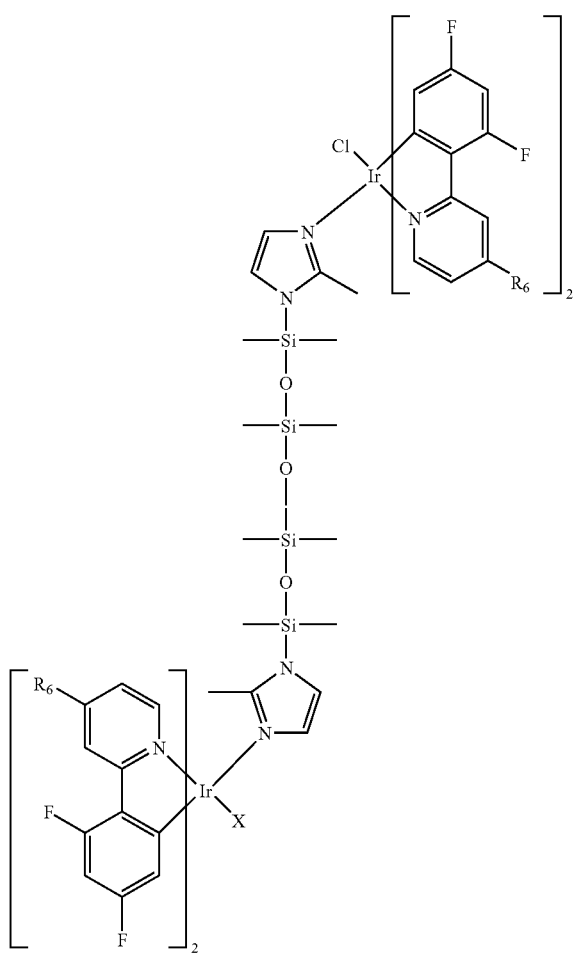

wherein R$_6$ is a $C_{1-12}$ alkyl group or —N(R)$_2$ where R is a $C_{1-12}$ alkyl group and X is F, Cl, Br, I, CN, CN(R), SCN, or OCN;

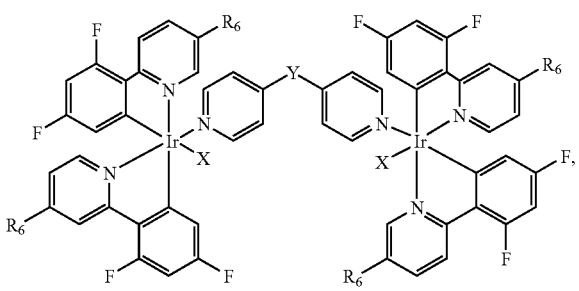

wherein R$_6$ is a $C_{1-12}$ alkyl group or —N(R)$_2$ where R is a $C_{1-12}$ alkyl group; X is F, Cl, Br, I, CN, CN(R), SCN, or OCN; and Y is a $C_{1-12}$ alkylene group, a $C_{6-20}$ arylene group, a $C_{3-20}$ heteroarylene group, or a carbonyl group.

8. The organometallic complex of claim 1, wherein the organometallic compound is selected from the group consisting of compounds represented by Formulas 3 through 7:

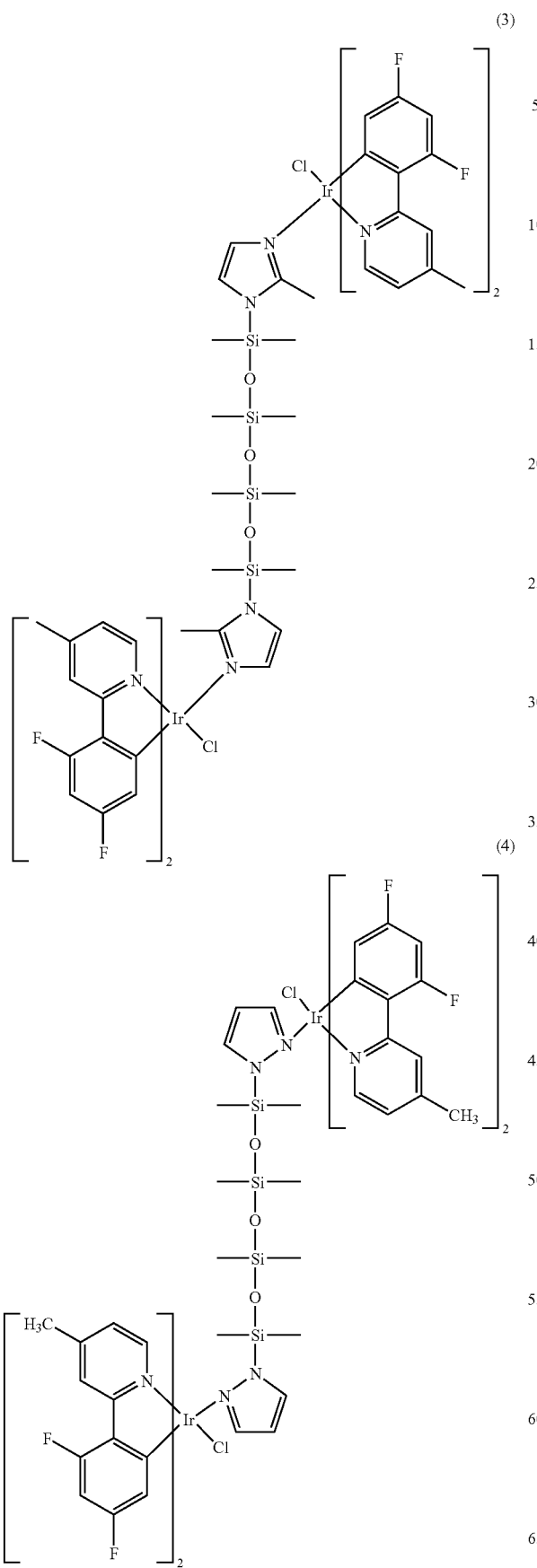
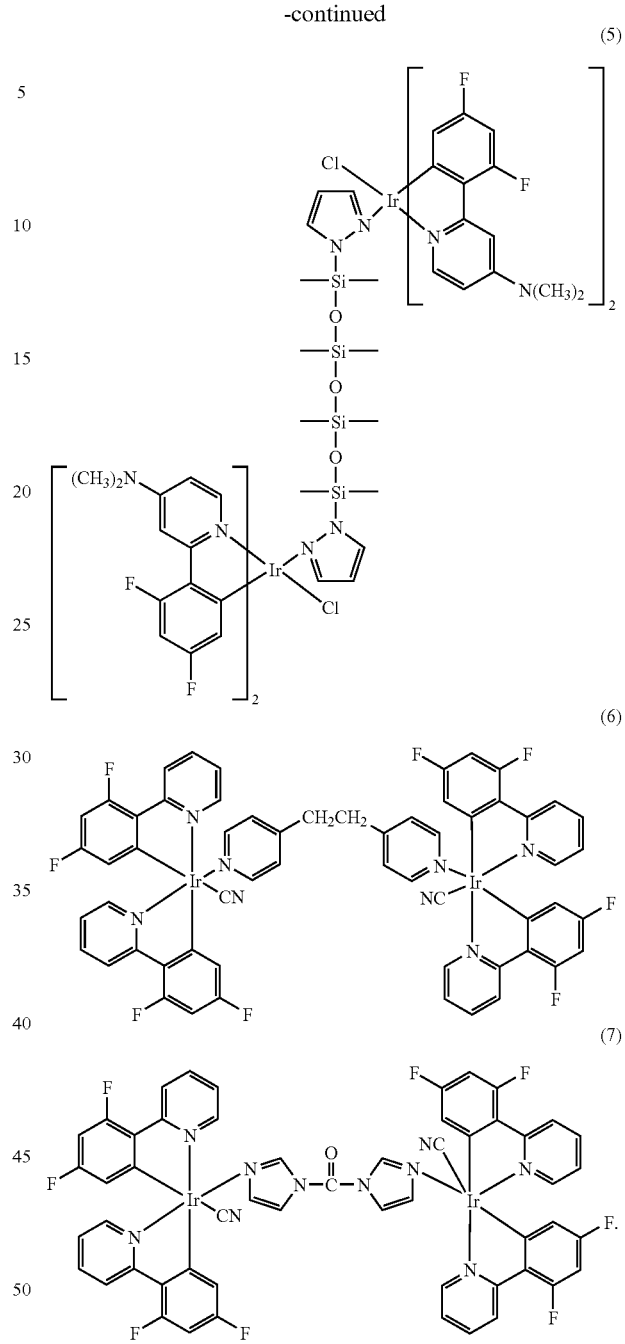
9. An organic electroluminescent device, comprising:
a pair of electrodes; and
an organic layer interposed between said pair of electrodes, the organic layer comprising the binuclear organometallic complex represented by Formula 1:
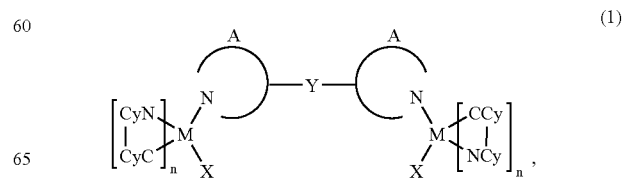

wherein M is a metal selected from the group consisting of Ir, Os, Pt, Pb, Re, Ru, and Pd;

CyN is a substituted or unsubstituted $C_3$-$C_{60}$ heterocyclic group containing nitrogen bonded to M, or a substituted or unsubstituted $C_3$-$C_{60}$ heteroaryl group containing nitrogen bonded to M;

CyC is a substituted or unsubstituted $C_4$-$C_{60}$ carbocyclic group containing carbon bonded to M, a substituted or unsubstituted $C_3$-$C_{60}$ heterocyclic group containing carbon bonded to M, a substituted or unsubstituted $C_3$-$C_{60}$ aryl group containing carbon bonded to M, or a substituted or unsubstituted $C_3$-$C_{60}$ heteroaryl group containing carbon bonded to M;

alternatively, CyN-CyC is represented by one of Formulas:

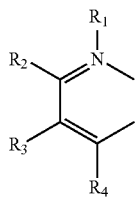
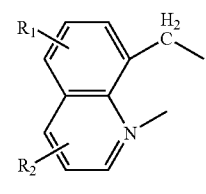
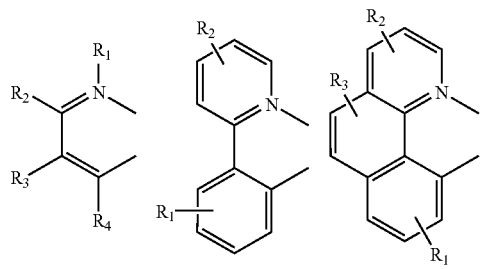

wherein each of $R_1$, $R_2$, $R_3$ and $R_4$, is indenendently a mono substituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group;

Y is a linker connecting two mononuclear organometallic complexes to each other;

A is a group containing nitrogen bonded to M;

X is a monoanionic monodentate ligand; and n is 1 or 2.

10. The organic electroluminescent device of claim 9, wherein the organic layer further comprises at least a compound selected from the group consisting of at least one polymer host, a mixture of a polymer host and a low molecular weight molecule host, a low molecular weight molecule host, and non-luminous polymer matrix.

11. The organic electroluminescent device of claim 9, wherein the organic layer further comprises a green luminescent material and a red luminescent material.

12. The organic electroluminescent device of claim 9, wherein the CyN-CyC is represented by one of the following formulas:

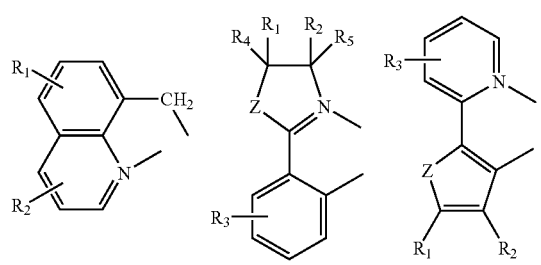
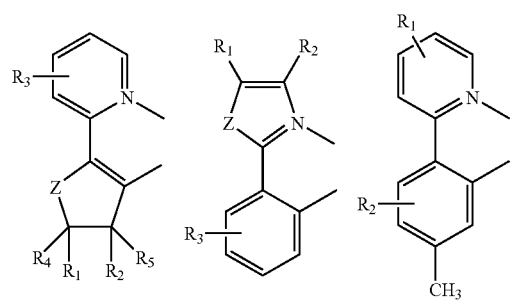
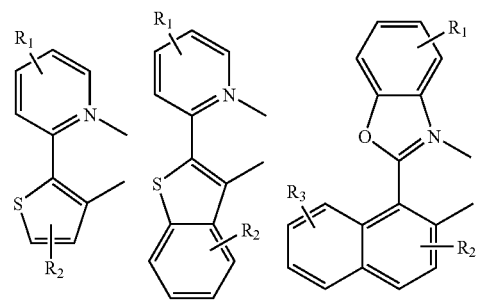
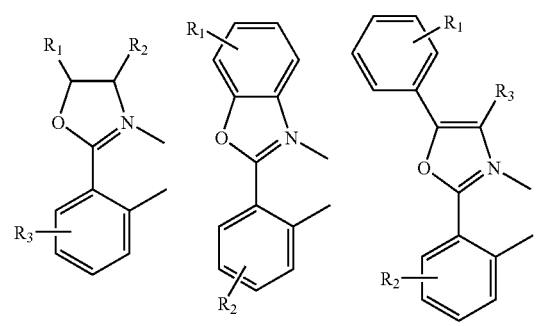

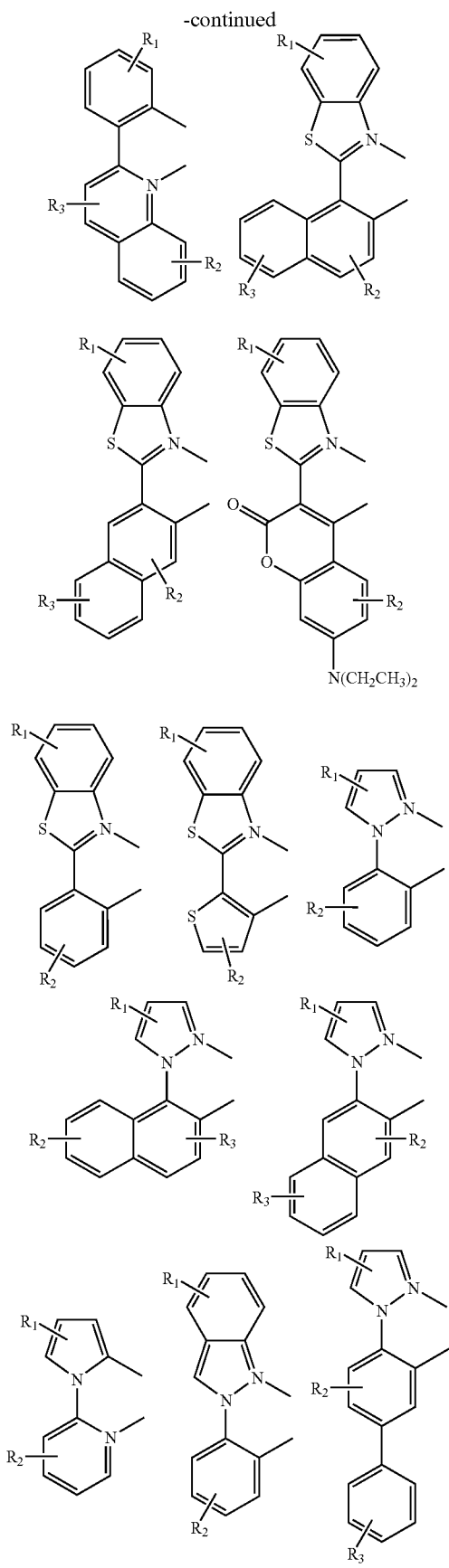

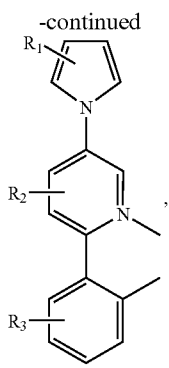

wherein each of $R_1$, $R_2$, $R_3$, $R_4$, and $R_5$ is independently selected from the group consisting of a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$ where R$_0$ is hydrogen or a $C_1$-$C_{20}$ alkyl group.

13. The organic electroluminescent device of claim 9, wherein A is derived from one selected from the group consisting of substituted or unsubstituted triethylamine, propylamine, cyclohexylamine, pyrrolidine, pyrroline, piperidine, pyrimidine, indole, azaindole, carbazole, indazole, norharman, harman, aniline, imidazole, oxazole, thiazole, pyrazole, pyrrole, benzimidazole, benzotriazole, benzoxazole, benzothiazole, benzoselenazole, benzothiadiozole, isoxazole, isothiazole, oxadiazole, thiadiazole, anthranyl, triazine, benzisoxazole, pyrazine, quinoline, benzoquinoline, acridine, thiazoline, quinuclidine, imidazoline, oxazoline, thiazoline, and isoquinoline.

14. The organic electroluminescent device of claim 12, wherein X is selected from the group consisting of F, Cl, Br, I, CN, CN(R), SCN, and OCN, and R is a substituted or unsubstituted $C_1$-$C_{20}$ alkyl group.

15. The organic electroluminescent device of claim 9, wherein Y is a $C_1$-$C_{20}$ alkylene group, a $C_6$-$C_{20}$ arylene group, a $C_1$-$C_{20}$ heteroalkylene group, a $C_2$-$C_{20}$ heteroarylene group, a $C_3$-$C_{20}$ heteroarylalkylene group, a carbonyl group, or a group derived from compounds selected from the group consisting of symmetrical triarylamines, asymmetrical triarylamines, phenylenevinylenes, polyfluorenes, polythiophenes, vinylcarbazoles, ethylene dioxythiophenes, silanes, siloxanes, and derivatives of thereof.

16. The organic electroluminescent device of claim 9, wherein M is Ir or Pt.

17. The organic electroluminescent device of claim 9, wherein the organometallic complex is represented by Formula 8 or Formula 9:

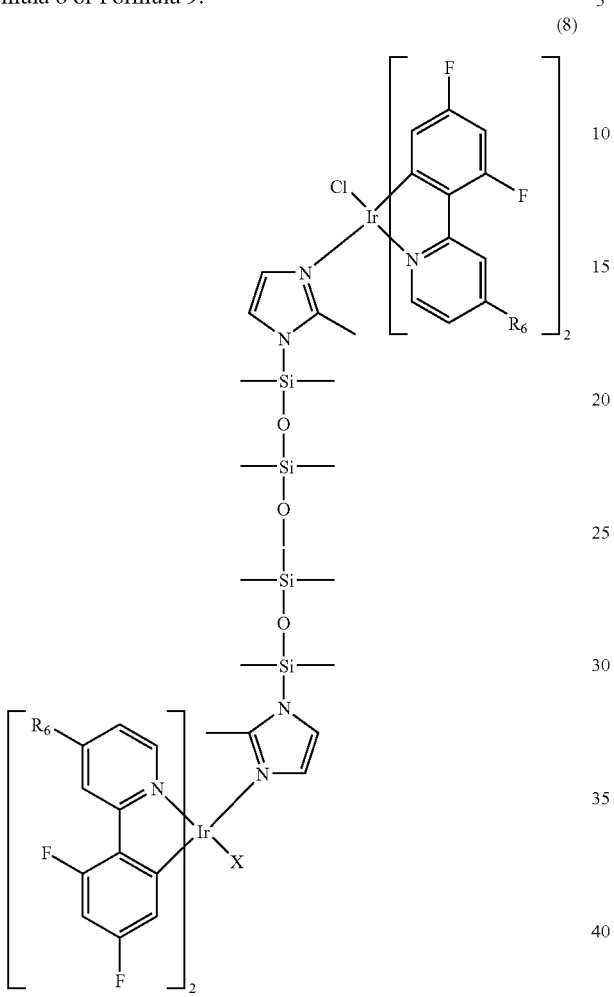

wherein $R_6$ is a $C_{1-12}$ alkyl group or $-N(R)_2$ where R is a $C_{1-12}$ alkyl group and X is F, Cl, Br, I, CN, CN(R), SCN, or OCN;

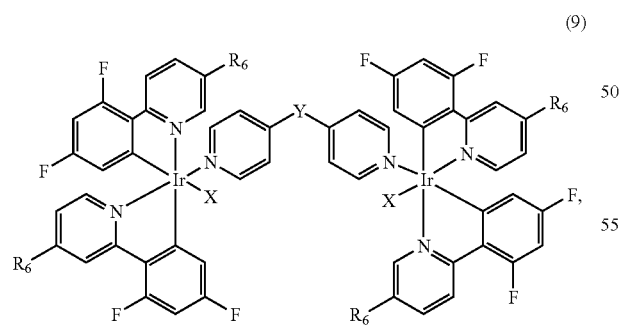

wherein $R_6$ is a $C_{1-12}$ alkyl group or $-N(R)_2$ where R is a $C_{1-12}$ alkyl group; X is F, Cl, Br, I, CN, CN(R), SCN, or OCN; and Y is a $C_{1-12}$ alkylene group, a $C_{6-20}$ arylene group, a $C_{3-20}$ heteroarylene group, or a carbonyl group.

18. The organic electroluminescent device of claim 9, wherein the organometallic compound is selected from the group consisting of compounds represented by Formulas 3 through 7:

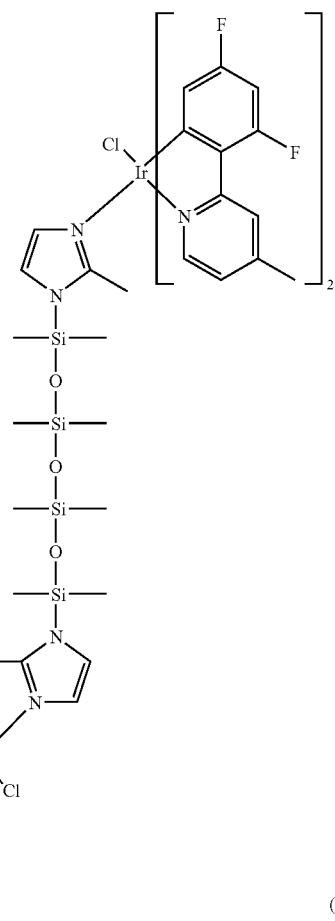

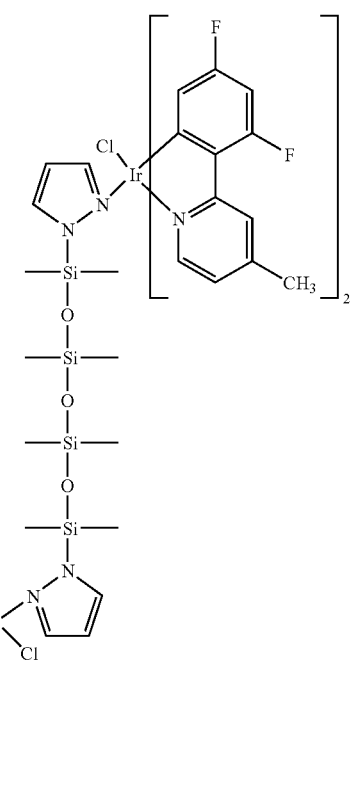

-continued

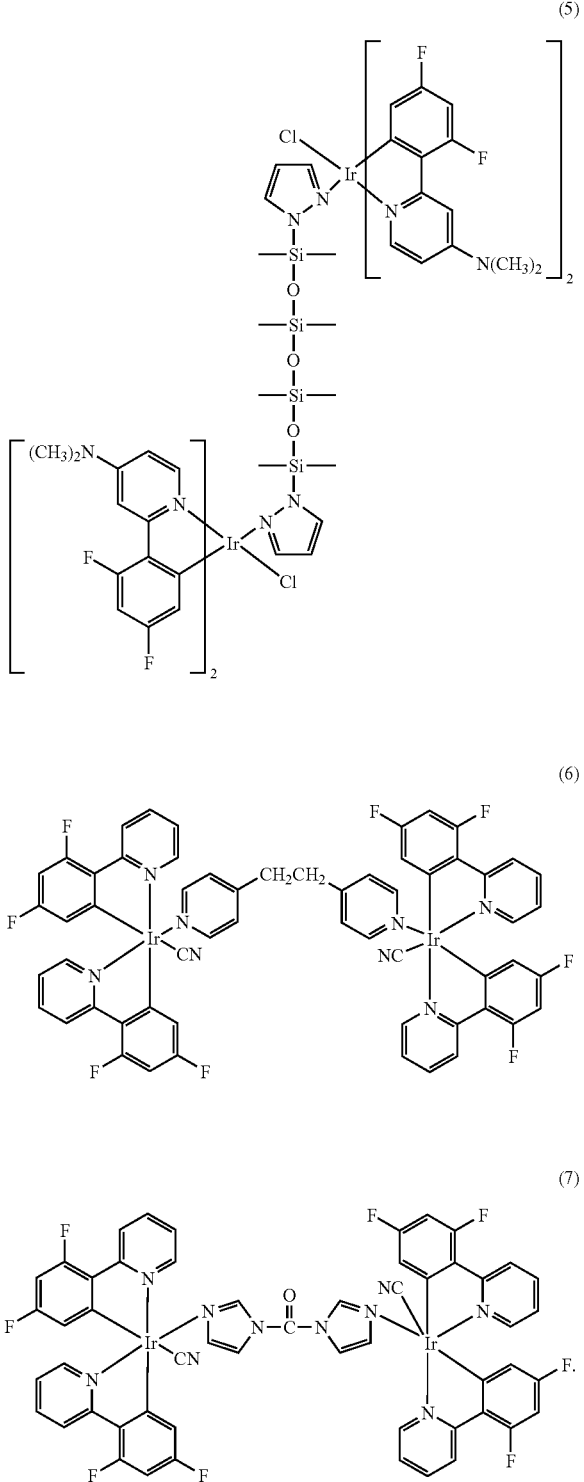

19. The organic electroluminescent device of claim 9, wherein the organic layer includes an electroluminescent layer, and the concentration of the binuclear organometallic complex represented by Formula 1 is in a range of 1 to 30 parts by weight based on 100 parts by weight of the total weight of the electroluminescent layer.

20. An organic electroluminescent device, comprising:
a pair of electrodes; and
an organic layer interposed between said pair of electrodes, the organic layer comprising the binuclear organometallic complex represented by Formula 1:

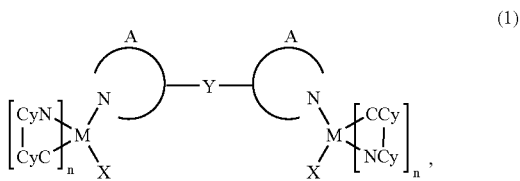

wherein M is a metal selected from the group consisting of Ir, Os, Pt, Pb, Re, Ru, and Pd;
Y is a linker connecting two mononuclear organometallic complexes to each other;
A is a group containing nitrogen bonded to M;
X is a monoanionic monodentate ligand;
n is 1 or 2; and
CyN-CyC is represented by one of the following formulas:

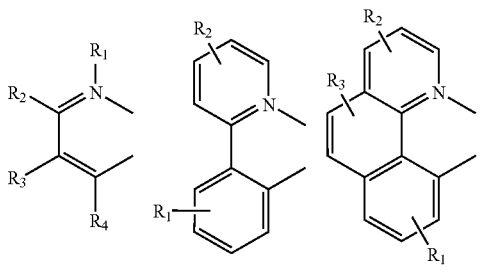

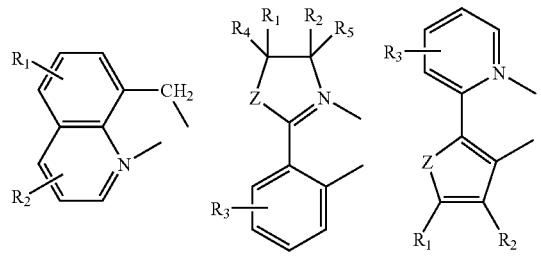

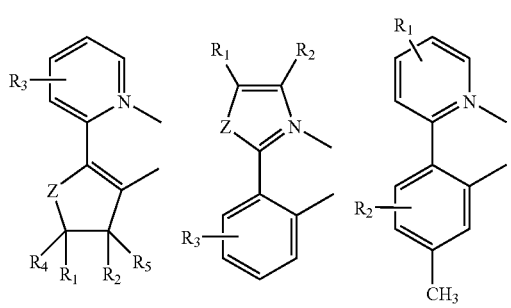

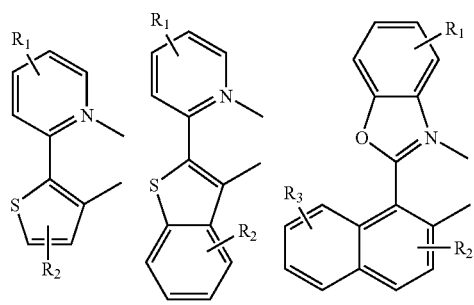

-continued

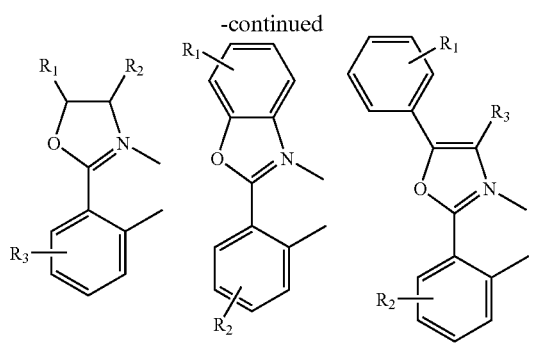

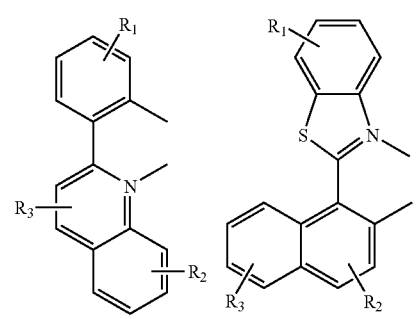

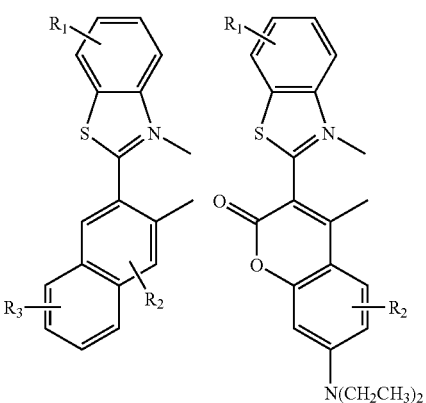

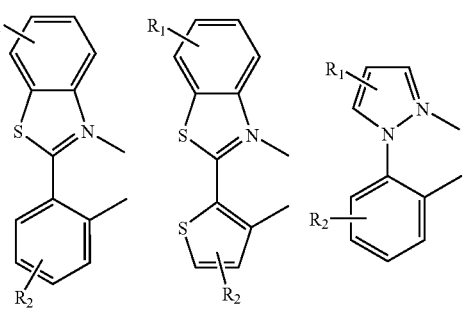

-continued

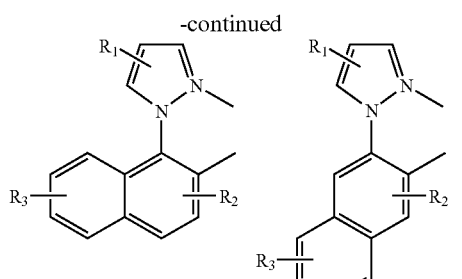

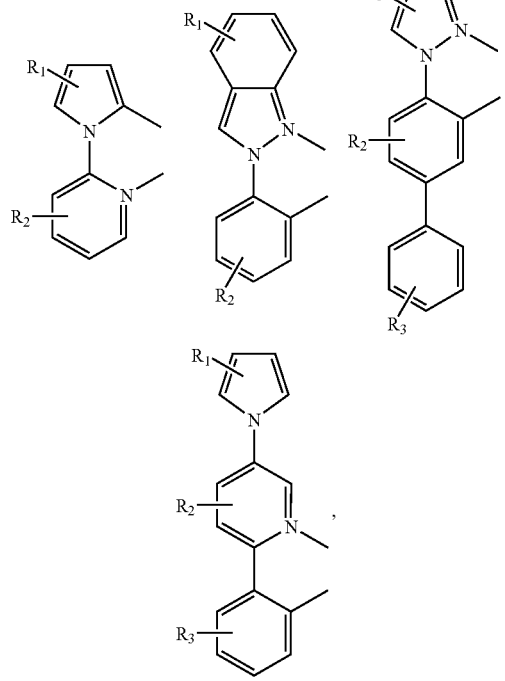

wherein each of $R_1$, $R_2$, $R_3$, $R_4$, and $R_5$ is independently selected from the group consisting of a monosubstituted or polysubstituted group, and is selected from the group consisting of hydrogen, a halogen atom, —OR, —N(R)$_2$, —P(R)$_2$, —POR, —PO$_2$R, —PO$_3$R, —SR, —Si(R)$_3$, —B(R)$_2$, —B(OR)$_2$, —C(O)R, —C(O)OR, —C(O)N(R), —CN, —NO$_2$, —SO$_2$, —SOR, —SO$_2$R, —SO$_3$R, a $C_1$-$C_{20}$ alkyl group, and a $C_6$-$C_{20}$ aryl group, where R is hydrogen, a substituted or unsubstituted $C_1$-$C_{20}$ alkyl group, a substituted or unsubstituted $C_1$-$C_{10}$ alkoxy group, a substituted or unsubstituted $C_2$-$C_{20}$ alkenyl group, a substituted or unsubstituted $C_2$-$C_{20}$ alkynyl group, a substituted or unsubstituted $C_1$-$C_{20}$ heteroalkyl group, a substituted or unsubstituted $C_6$-$C_{40}$ aryl group, a substituted or unsubstituted $C_7$-$C_{40}$ arylalkyl group, a substituted or unsubstituted $C_7$-$C_{40}$ alkylaryl group, a substituted or unsubstituted $C_2$-$C_{40}$ heteroaryl group, and a substituted or unsubstituted $C_3$-$C_{40}$ heteroarylalkyl group; and Z is S, O, or NR$_0$ where R$_0$ is hydrogen or a $C_1$-$C_{20}$ alkyl group.

* * * * *